United States Patent [19]
Nappholz

[11] Patent Number: 5,755,740
[45] Date of Patent: May 26, 1998

[54] PACEMAKER WITH AUTOMATIC CALIBRATION OF THE RESPONSE OF MULTIPLE SENSORS

[76] Inventor: Tibor Nappholz, 8524 E. Jamison Ave., Englewood, Colo. 80112

[21] Appl. No.: 956,764

[22] Filed: Oct. 22, 1997

Related U.S. Application Data

[63] Continuation of Ser. No. 701,377, Aug. 22, 1996, abandoned.

[51] Int. Cl.[6] .................................................. A61N 1/365
[52] U.S. Cl. .................................................. 607/18; 607/19
[58] Field of Search .................................................. 607/17–24

[56] References Cited

U.S. PATENT DOCUMENTS

| | | |
|---|---|---|
| 4,702,253 | 10/1987 | Nappholz et al. |
| 5,044,366 | 9/1991 | Alt .................................................. 607/20 |
| 5,065,759 | 11/1991 | Begemann et al. .................................................. 607/19 |
| 5,097,831 | 3/1992 | Lekholm .................................................. 607/20 |
| 5,282,839 | 2/1994 | Roline et al. .................................................. 607/19 |
| 5,376,106 | 12/1994 | Stahmann et al. .................................................. 607/18 |
| 5,562,711 | 10/1996 | Yerich et al. .................................................. 607/18 |

*Primary Examiner*—William E. Kamm
*Assistant Examiner*—George R. Evanisko
*Attorney, Agent, or Firm*—Gottlieb,Rackman & Reisman

[57] ABSTRACT

In a dual sensor pacer/defibrillator the output of a metabolic sensor is used to calibrate the output a second sensor over a long time period. In this manner the two sensor outputs track accurately the metabolic demand of the patient and no recalibration by a clinician is necessary.

6 Claims, 5 Drawing Sheets

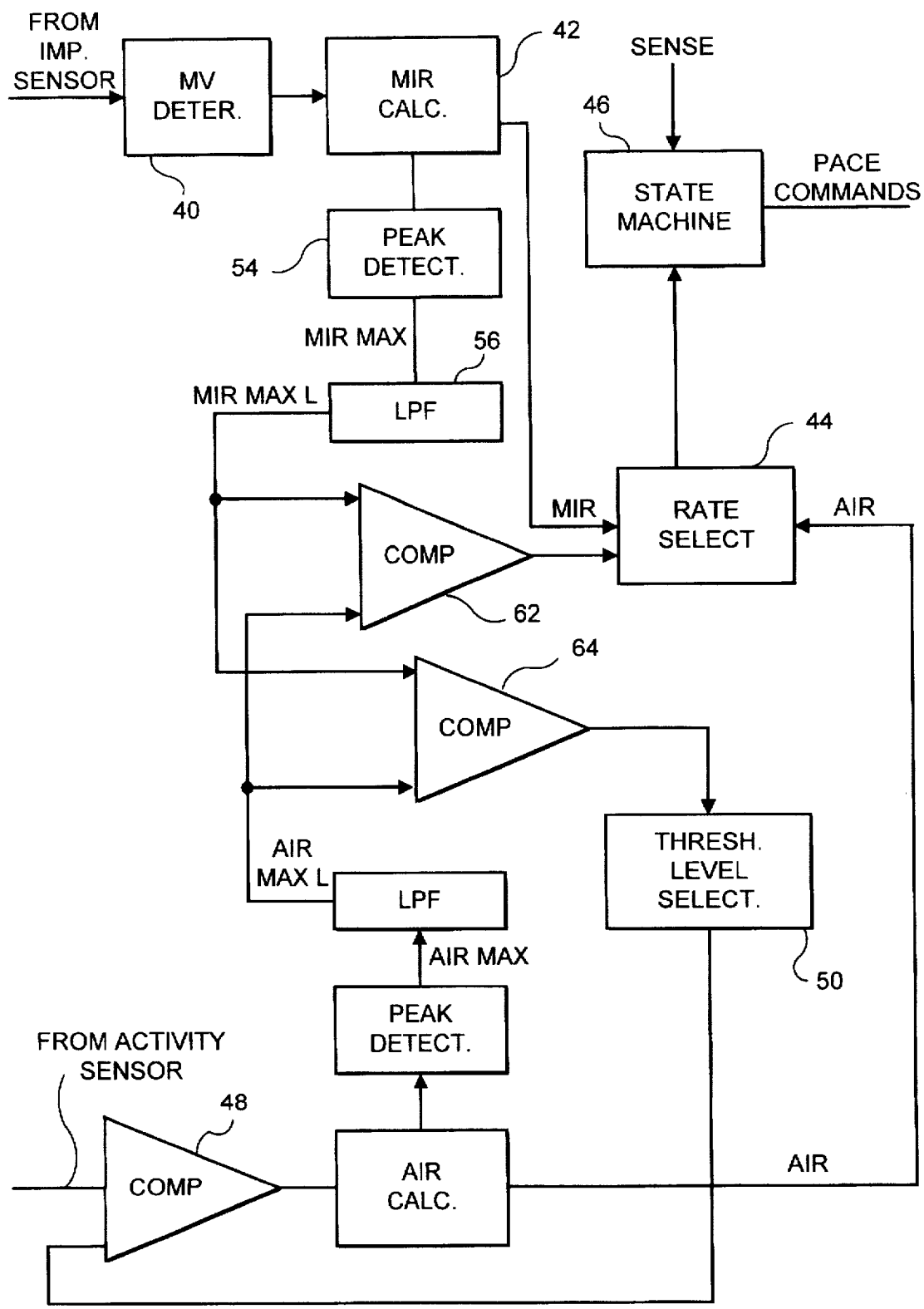
F I G. 4

PACEMAKER WITH AUTOMATIC CALIBRATION OF THE RESPONSE OF MULTIPLE SENSORS

This is a continuation of application Ser. No. 08/701,377 filed on Aug. 22, 1996 now abandoned.

A. FIELD OF THE INVENTION

This invention relates to pacemakers, with at least two sensors having different response times, and more particularly to a rate-responsive pacemaker adapted to automatically correlate the responses of the two sensors to compensate for the differences in their response to an exercise/ activity period with relatively fast onset.

B. BACKGROUND OF THE INVENTION

In this application the term 'pacemaker' is used generically to designate implantable cardiac devices, including devices which can provide only pacing functions, as well as devices which may also provide cardioversion and/or defibrillation functions.

Rate responsive pacemakers are pacemakers which measure a physiological parameter indicative of the metabolic demand of blood on a patient's heart, and based on this parameter, derive a corresponding pacing rate in a manner selected to imitate the response of a healthy heart. Such a parameter may be for example minute ventilation which is sensed by an appropriate sensor. In many pacemakers, it is desirable to use a second sensor to measure a different parameter, for example related to the level of physical activity of the patient. This second sensor may be for instance an accelerometer or piezoelectric sensor adapted to provide an output indicative of the actual physical movement level of a patient. A rate responsive sensor of this kind is disclosed in commonly assigned application Ser. No. 309,790 filed Sep. 21, 1994. The outputs of the sensors are then analyzed to determine, for example, if an increase in metabolic demand on the heart is from a physiological or pathological source.

A problem associated with dual sensor pacemakers is that the two sensors and associated circuitry have different response times and maximum rates because of various inherent delays and threshold levels. More specifically, metabolic demand sensors while more accurate, may be slower to respond to sudden exercise onset than physical activity sensors. In order to calibrate the sensors, the patient is asked, after implantation, to perform a preselected exercise regimen, such as walking briskly for a predetermined distance or for a predetermined time. However, this calibration is insufficient to compensate for sensor responses associated with an exercise period characterized by a sudden onset. In addition, it is very time consuming and hence expensive.

OBJECTIVES AND SUMMARY OF THE INVENTION

In view of the abovementioned disadvantages of the prior art it is an objective of the present invention to provide a dual sensor pacemaker in which a metabolic demand indicator and a physical activity indicator are automatically calibrated without the need of any special regime by the patient or physician.

A further objective is to provide a dual sensor pacemaker in which the activity sensor output is automatically calibrated over an extended time period to the most frequent physical activity of the patient.

A further objective is to provide a dual sensor pacemaker wherein a dual indicated rate is determined from both a metabolic demand and a physical activity sensor to automatically compensate for a sudden onset of physical activity onset.

Other objectives and advantages of the invention shall become apparent from the following description of the invention.

Briefly, a pacemaker constructed in accordance with this invention includes means for sensing cardiac activity, means for generating cardiac pulses on demand, and dual sensing means for sensing a first parameter indicative of metabolic demand and a second parameter indicating level of physical activity. The two parameters are covered into corresponding rates MIR and AIR. The sensitivity of the physical activity sensor means is adjusted so that the peak value of AIR is within 20% of the peak value of the MIR. The two rates are monitored and a dual sensor rate DIR is derived wherein said DIR is defined as the larger of MIR and AIR. In this manner, in this response to onset of exercise, the dual sensors are used to generate a rate which closely resembles the sinus rate.

BRIEF DESCRIPTION OF THE FIGURES

FIG. 4 shows a block diagram for the controller of FIG. 1; and

DETAILED DESCRIPTION OF THE INVENTION

Figure 1:
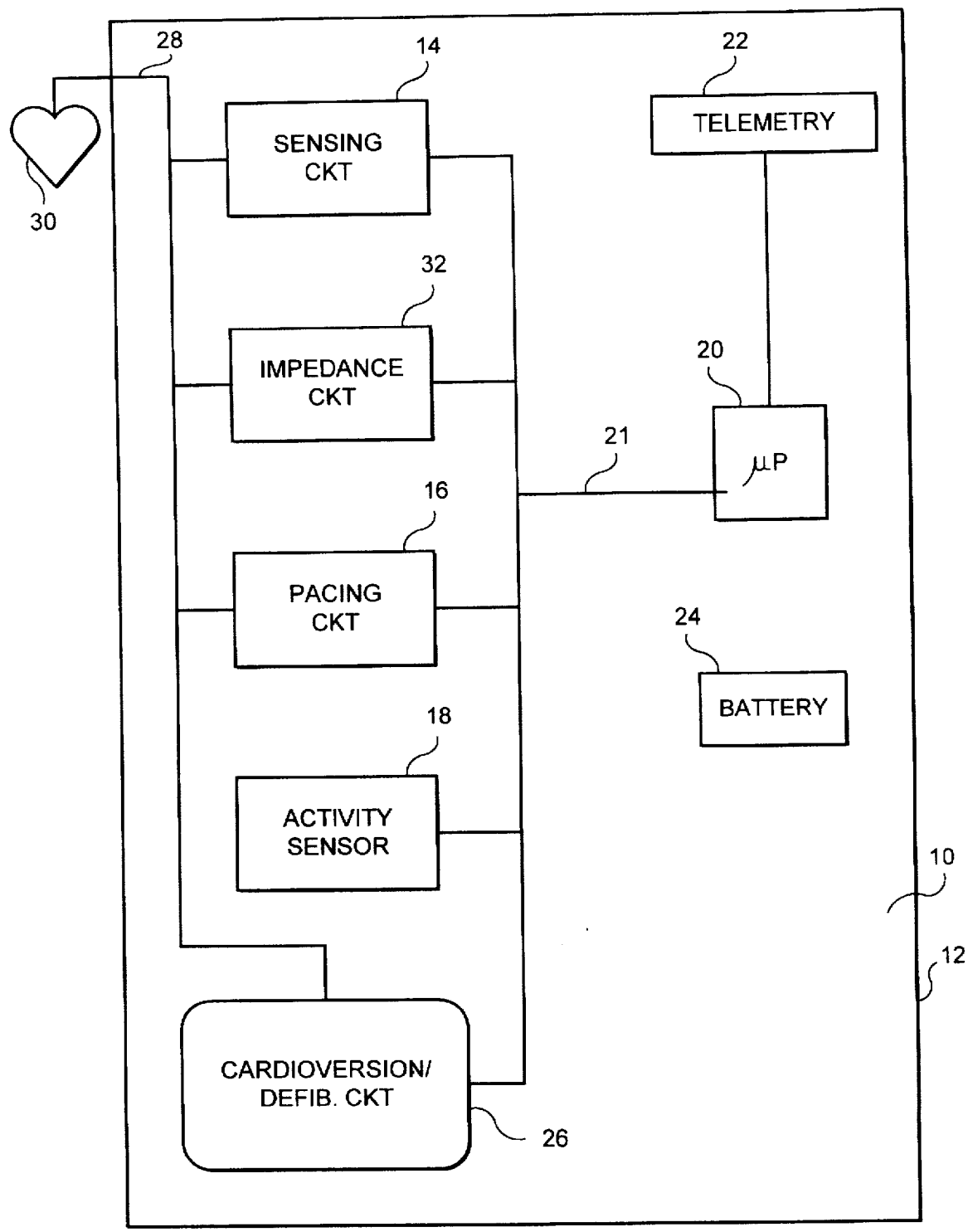
FIG. 1 shows a block diagram of a pacemaker constructed in accordance with this invention.

Referring now to FIG. 1, a pacemaker 10 constructed in accordance with this invention, includes an implantable housing 12 containing a sensing circuit 14, a pacing circuit 16 and an activity sensor 18. All three of these elements are coupled by a bus 21 to a controller 20 which is typically a microprocessor. The controller 20 is connected to a telemetry circuit 22 for communication with the outside world. Power to these components is provided by a battery 24.

The term pacemaker is used herein to cover implantable cardioversion devices as well. If pacemaker 12 is in fact a cardioverter and/or defibrillator device then it may include cardioverter/defibrillator circuitry 26, also coupled to controller 20. One or more electrodes 28 are inserted into the heart 30 of a patient. These electrodes are coupled to the sensing circuit 14, pacing circuit 16 and cardioversion/ defibrillator circuitry 26, if present. Housing 12 further includes an impedance circuit 32 for determining the transthoracic impedance of the patient, usually measured between the distal end of one of electrodes 28 and the housing 12, as discussed more fully below. Impedance circuit 32 is also connected to controller 20 via bus 21.

Generally speaking the impedance circuit 32 measures the instantaneous transthoracic impedance of the patient and provides a signal corresponding to this measurement to the controller for indicating a metabolic demand such as differential minute volume, as set forth in U.S. Pat. No. 4,702,253. This parameter is mapped or converted by the controller into a corresponding metabolic indicated rate.

Similarly, the physical activity sensor 18 is used to measure the instantaneous physical activity of the patient. This parameter is used by controller 20 to determine the physical activity indicated rate by controller 20. These two indicated rates are combined by the controller into a dual indicated rate.

Various cardiac activities (such as intrinsic atrial and/or ventricular beats, depolarizations and so forth) are sensed by sensing circuit 14 and transmitted to the controller 20. The controller 20 uses this information and the dual indicated rate to determine the optimal pacing of the heart 30, and, to generate commands ordering pacing circuit to generate cardiac paces, if necessary as discussed below, in conjunction with FIGS. 3–5. The controller may also command cardioverting/defibrillator circuitry 26 to provide to heart 30 cardioversion and/or defibrillation pulses.

Figure 2:
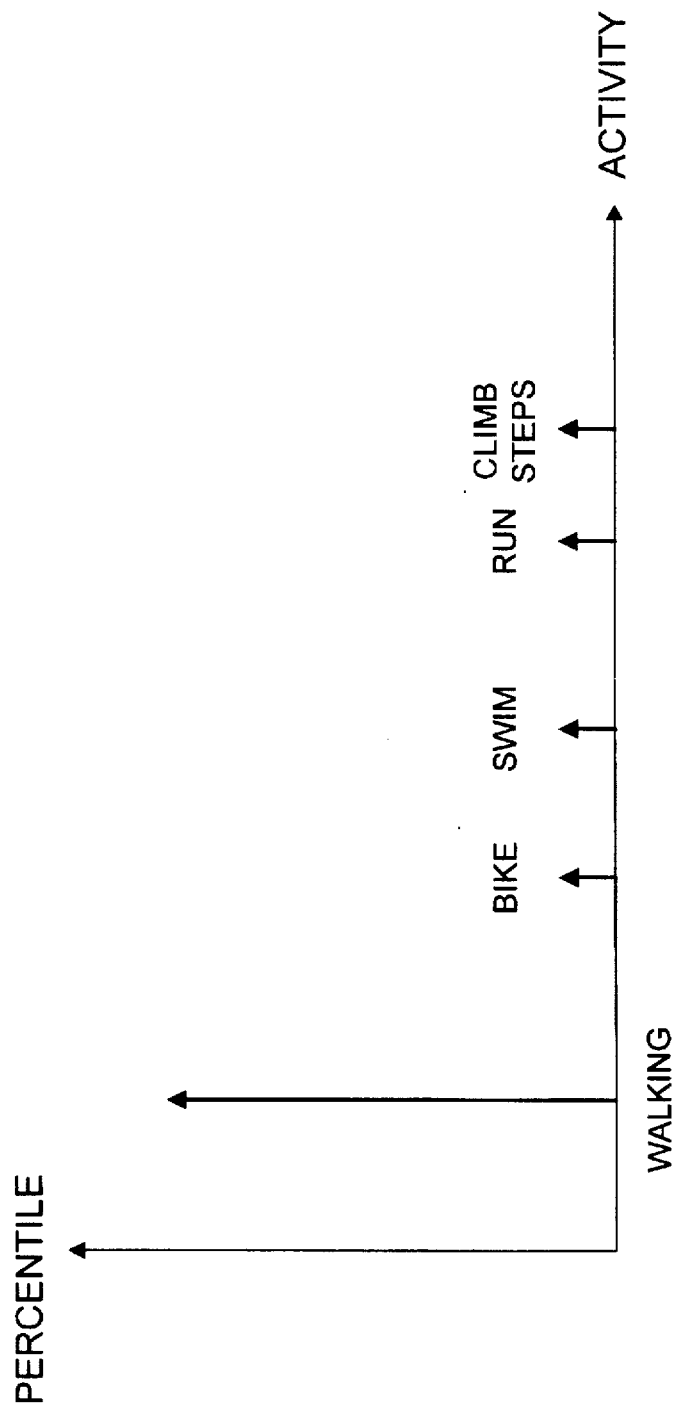
FIG. 2 shows graphically the percentile rating of various types of physical activities for a typical patient.

Typically, physical activity sensors, such as for example, accelerometers, count the number of times a certain parameter exceeds a preselected threshold in a unit of time, i.e., second, minute, hour, etc. This number is characteristic to the kind of physical activity. By far the most prevalent physical activity is walking. As shown in FIG. 2, the percentile level of physical activity for walking is several times the percentile levels for biking, swimming, running, climbing stairs, etc. In the present invention, a long term calibration is performed between the physical activity response of the pacemaker and the metabolic demand. Since in the long run, the most frequent physical activity is walking, the physical activity is automatically calibrated and optimized for this type of metabolism.

Figure 3:
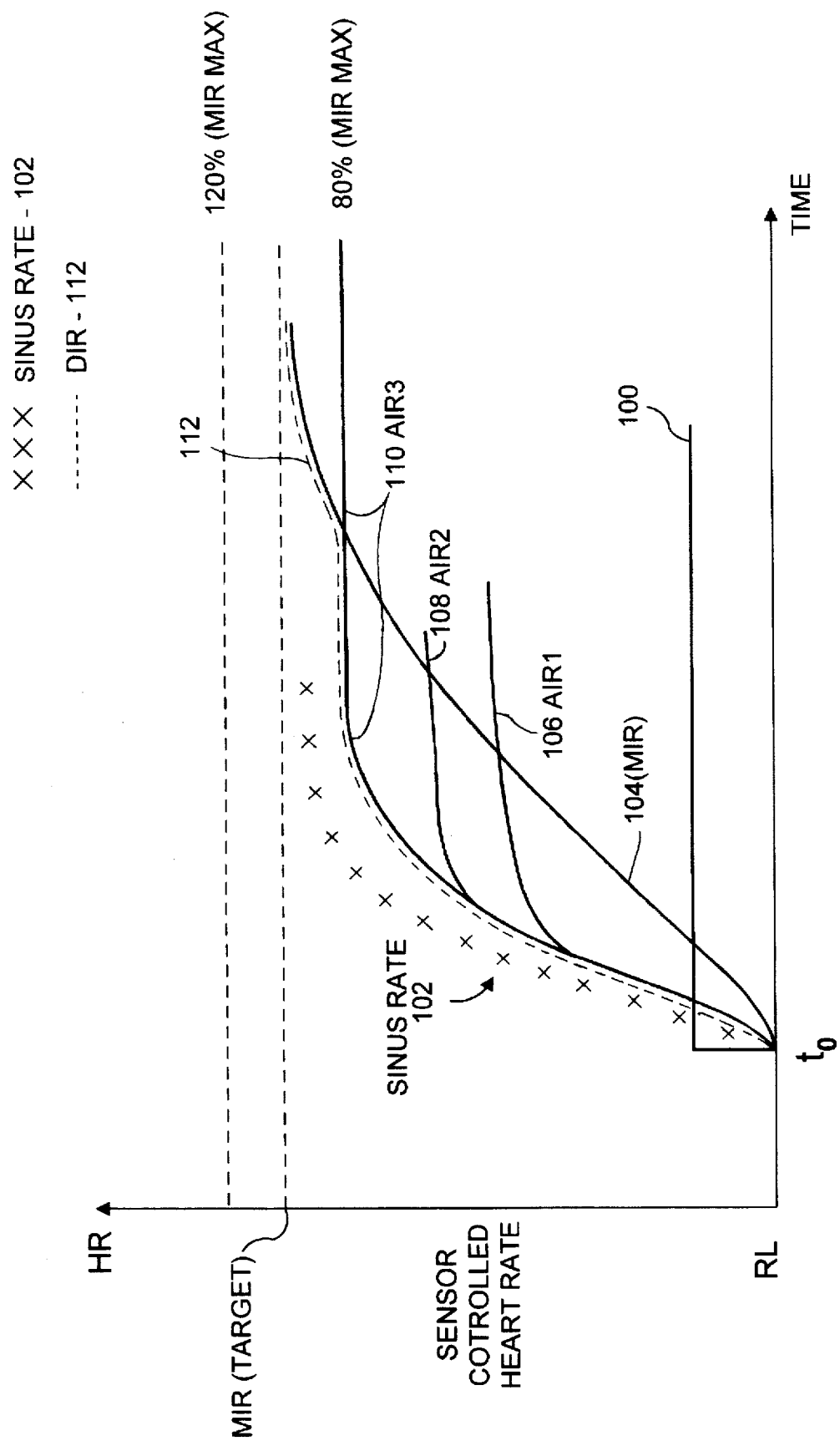
FIG. 3 shows graphically various indicated rates determined by the pacemaker of claim 1 as a function of time.

More specifically, in FIG. 3, curve 100 indicates a sudden onset of an exercise period by a patient. The normal sinus response (i.e., heart rate) to this onset is indicated by curve 102. As can be seen from FIG. 3, the curve 102 rises to its peak level fairly rapidly. The metabolic indicated rate (MIR) resulting from a metabolic demand parameter such as differential minute volume is shown in FIG. 3 by curve 104. As can be seen from this Figure, when compared to the curve for the sinus rate, the MIR curve 104 starts rising very slowly and reaches its peak level MIR max later than the sinus rate curve 102.

The activity indicated rate resulting from the physical activity sensor is generally faster than the MIR and its rate or rise in independent of its peak value.

This peak value depends on the sensitivity used in generating the parameter AIR. FIG. 3 shows three different curves 106, 108 and 110 corresponding to three rates AIR1, AIR2 and AIR3. While all three curves have an onset which is much faster than the onset of MIR (curve 104) AIR1 and AIR2 reach corresponding maximum levels which are much lower than the MIR MAX and hence they are clearly inappropriate. The third curve AIR3 rises to a level much closer than MIR MAX but it still fairly low. Therefore the sensitivity of the acceleration channel used for deriving AIR must be adjusted so that its peak level AIR MAX is the same of the peak level MIRMAX of curve 104.

One approach for obtaining this result is shown in FIG. 4. In this Figure, the output of the impedance circuit 32 is fed to a minute volume determining circuit 40. This circuit 40 is used to derive a metabolic demand parameter such as minute volume. The minute volume parameter is fed to a mapping circuit 42 for generating a corresponding metabolic indicated parameter MIR, as described, for example, in U.S. Pat. No. 4,702,253. The parameter MIR is fed to a rate selector 44 which also receives as its input an activity indicated rate AIR and selects one of these rates, or a combination of both, as described below. The output DIR of the rate selector 44 is fed to a state machine 46. The state machine also receives cardiac activity indication signals from sensing circuit 14 and in response to these parameters generates pacing commands for pacing circuit 16.

The parameter AIR is derived as follows. The output of activity sensor 34 is fed to a comparator 48. The comparator compares the sensor output to a threshold received from a threshold selector 50. If the sensor output exceeds this threshold than a signal is sent to AIR calculator 52 which in response calculates the AIR parameter previously discussed. This process is well known in the art, as described for example in U.S. Pat. No. 4,702,253 and therefore need not be described here in more detail.

Importantly, the parameter MIR is fed to a peak detector 54 which is used to detect the maximum level MIR MAX and feeds the same to a lowpass filter 56. The low-pass filter 56 has a very long time constant so that in effect accumulates and averages the value MIR MAX over several days to obtain a long term parameter MIR MAX L. The time constant may be for example from eight to thirty days.

Similarly the parameter AIR is fed to a peak detector 58 for detecting the level AIR MAX. This level is then fed to a second low pass filter 60 which also has a very long time constant for accumulating and averaging the level AIR MAX to generate a long term parameter AIR MAX L. The two outputs of the low pass filters 56, 60 are each fed to two comparators 64, 66. Comparator 64 is used to determine if the output of lowpass filter 60. In other words, the comparator 62 determines if the AIR MAX L is within a preselected range (i.e. ±20%) of MIR MAX L. This determination is sent to rate selector 44. If the two maximum long parameters MIR MAX L and AIR MAX L are comparable than the rate selector 44 combines the two rates MIR, AIR to obtained a dual sensor rate (DIR) which has preselected optimal characteristics. For example in order to obtain a rate with a fast onset, the rate selector may initially select DIR to follow AIR to a certain level and then switch over to MIR. Obviously other methods of combining the information from AIR and MIR may be used by selector 44.

Comparator 64 is used to adjust the threshold level of comparator 48 thereby adjusting its sensitivity. More particularly comparator 64 may be used to generate an up/down control signal C for the threshold level selector 50. For this purpose the two levels AIR MAX L and MIR MAX L are compared by the comparator 64. If MIR MAX L is larger compared than AIR MAX L than the level AIR MAX is too small. Accordingly an "up" command is sent to the threshold level selector 50 to raise the threshold sent to comparator 48 by an incremental amount. Of AIR MAX L and higher than MIR MAX L then a "down" command is sent to selector 50 to reduce the threshold for comparator 48 by an incremental value. In this manner the circuit slowly trains itself to adjust the two rates AIR, MIR to the same maximum levels automatically.

Figure 5:
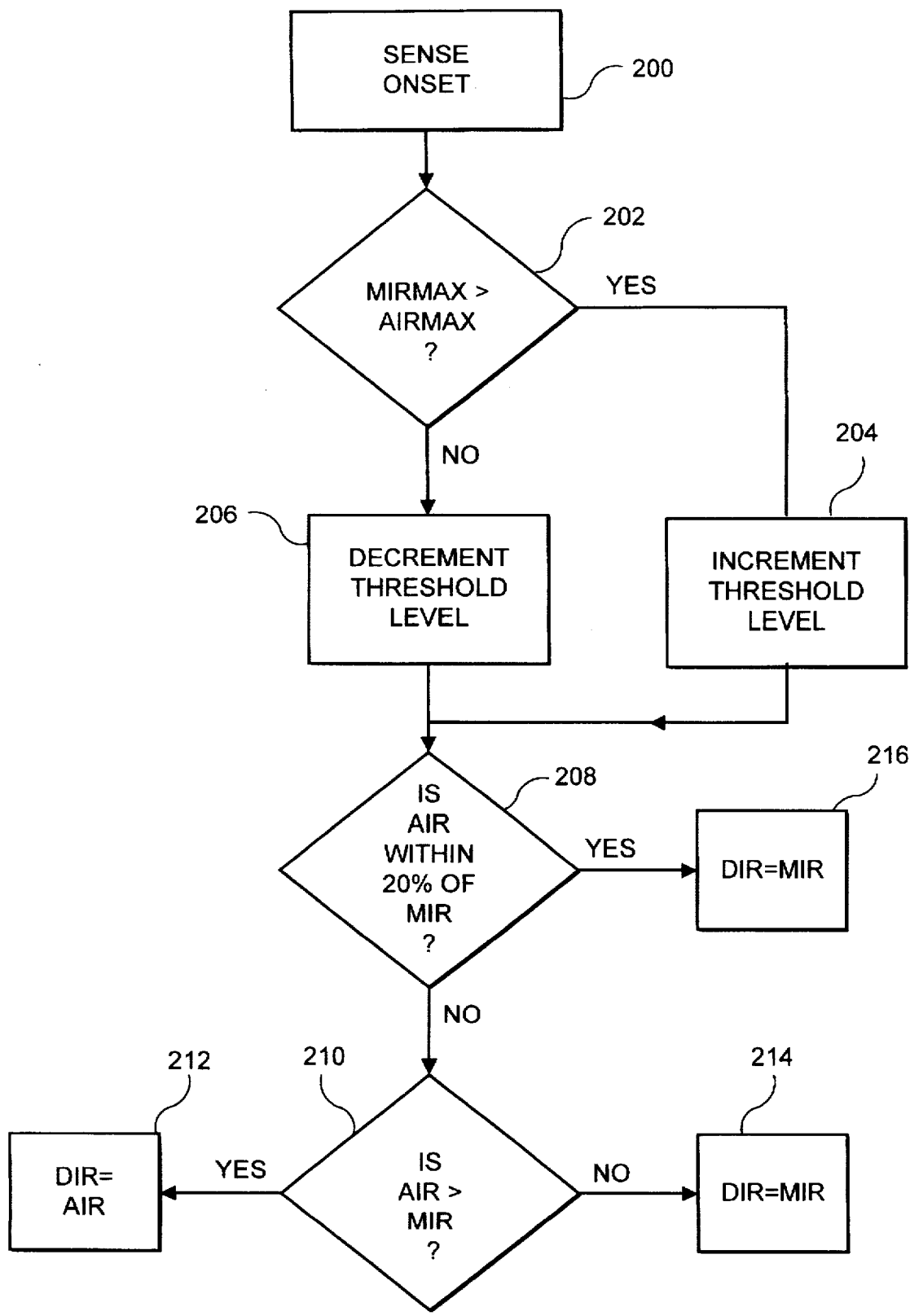
FIG. 5 shows a flow chart for the indicated rate combiner of FIG. 4.

The operation of the controller 20 is summarized in the flow chart of FIG. 5. Assume that initially the patient is at rest so that his heart rate is at a rest level RL. The onset of physical activity is sensed by the rate selector 44 as a rise in either the MIR or AIR parameter in step 200. As soon as this onset is sensed, in step 202 comparator 64 determines whether MIRMAX is greater than AIRMAX. If it is greater than in step 204 the threshold level selector receives a command to increment the threshold level. If the MIRMAX is smaller than AIRMAX then in step 206 the selector receives a command to decrement the threshold level.

In either case, in step 208 comparator 62 determines whether AIRMAX is within 20% of MIRMAX. If it is, then the rate selector 44 selects a DIR profile which is combination of AIR and MIR. For example, the rate selector may select a profile determined by the following rules:

(1) For AIR>MIR, DIR=AIR;
(2) For AIR<MIR, DIR=MIR.

Curve 112 in FIG. 3 illustrate the profile for DIR in accordance with the rules described above.

This process maybe implemented as follows. In step 210 the selector 44 compares MIR to AIR. IF AIR is larger, in step 212 the selector sets DIR to AIR. The selector continues checking the two rates until MIR becomes larger than AIR. At this point, in step 214 DIR is set to MIR.

Getting back to step 208, if AIRMAX is outside the designated range than sensitivity of the accelerator sensing is too small. Until the sensitivity increases to an acceptable level, the selector 44 sets DIR to follow MIR.

In this manner the controller calibrates the output of the acceleration channel to insure that its sensitivity is commensurate with the metabolic rate parameter. This sensitivity is continuously updated and it automatically adapts to the level of physical activity of the patient. While the controller is described as having discrete components, it should be understood that it is best implemented by a microprocessor.

Although the invention has been described with reference to a preferred embodiment, it is to be understood that this embodiment is merely illustrative of the application of the principles of the invention. Accordingly, the embodiment described in particular should be considered exemplary, not limiting, with respect to the following claims.

I claim:

1. A multiple sensor pacemaker/defibrillator for insertion in a patient, comprising:

a first sensor generating a first parameter correlated with a metabolic demand of said patient;

a first converter converting said first parameter into a first indicated rate in accordance with a first gain;

a second sensor for generating a second parameter related to a physical activity of said patient;

a second converter for converting said second parameter into a second indicated rate in accordance with a second gain;

a comparator comparing said first and second rates between an upper and a lower limit to determine which is larger;

an adjustment circuit adjusting over an extended time period said second gain using said first parameter as a calibration target for calibrating said second parameter to automatically adjust to the biological needs of the patient;

a selector for selecting a dual rate by selecting the larger of said metabolic and activity rates as determined by said comparator; and a pace generator for generating pacing pulses at said combined rate;

whereby the gains of the converters are automatically calibrated.

2. A dual sensor implantable pacemaker for implantation in a patient, said pacemaker comprising:

a metabolic sensor sensing a metabolic demand of said patient and generating in response a metabolic demand parameter;

a first converter converting said metabolic demand parameter into a corresponding demand pacing rate, said demand pacing rate having a demand peak rate level;

an activity sensor sensing a physical activity of said patient and generating in response a physical activity parameter, said activity sensor having a sensitivity;

a second converter converting said physical activity parameter into a corresponding activity pacing rate, said activity pacing rate having an activity peak rate level dependent on said sensitivity;

a combining circuit for combining said activity pacing rate and said demand pacing rate into a dual pacing rate by selecting the larger of said activity pacing rate and said demand pacing rate between a predetermined lower and a predetermined upper pacing limit;

a pacing generator generating pacing pulses in response to said dual pacing rate;

a comparator comparing said activity peak rate level and said demand peak rate level; and a sensitivity adjusting circuit adjusting said sensitivity if said activity peak rate level is outside a preselected range of said demand peak rate level as determined by said comparator.

3. The pacemaker of claim 2 further comprising a first and a second accumulator for accumulating said demand and said activity peak rate levels respectively to determine corresponding long term activity and demand peak levels, and wherein comparator compares said long term peak levels.

4. The pacemaker of claim 3 wherein said accumulators accumulate said peak levels over several days.

5. An implantable pacemaker comprising:

a metabolic sensor for generating a metabolic parameter indicative of metabolic demand of a patient;

a first convertor generating a metabolic pacing rate from said metabolic parameter;

a first peak detector detecting a metabolic peak rate for said metabolic pacing rate;

a first accumulator accumulating said metabolic peak rate to generate a long term metabolic peak rate level;

an activity sensor having a sensitivity and generating an activity parameter indicative of a physical activity of said patient;

a second convertor generating an activity pacing rate corresponding to said activity parameter;

a second peak detector detecting an activity peak rate for said activity pacing rate;

a second accumulator generating a long term peak activity rate level;

a comparator comparing said metabolic and activity long term peak rate levels;

an adjustor circuit adjusting said sensitivity if said comparator indicates a difference between said long term peak rate levels until said peak activity rate level is within a preselected range of said peak metabolic rate;

a combiner circuit for combining said metabolic and said activity pacing rates to define a dual pacing rate by selecting the larger of said metabolic and said activity pacing rates over a predetermined pacing range; and a pacing generator generating pacing pulses in accordance with said dual pacing rate.

6. The pacemaker of claim 5 wherein said combiner circuit ignores said activity pacing rate if said peak activity level is outside said range.

* * * * *